United States Patent
Odogba et al.

(10) Patent No.: US 7,369,711 B2
(45) Date of Patent: May 6, 2008

(54) ASYNCHRONOUS CALIBRATION AND CORRECTION OF A SOLID-STATE DETECTOR

(75) Inventors: Jibril Odogba, Wales, WI (US); Kenneth Scott Kump, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 728 days.

(21) Appl. No.: 10/788,070

(22) Filed: Feb. 26, 2004

(65) Prior Publication Data

US 2005/0190983 A1 Sep. 1, 2005

(51) Int. Cl.
G09G 3/36 (2006.01)
G06K 9/40 (2006.01)

(52) U.S. Cl. .................. 382/254; 382/128; 382/132

(58) Field of Classification Search ............. 382/128, 382/130, 132, 254
See application file for complete search history.

(56) References Cited

U.S. PATENT DOCUMENTS

| | | | |
|---|---|---|---|
| 5,657,400 A * | 8/1997 | Granfors et al. | 382/254 |
| 5,682,413 A | 10/1997 | Wong et al. | 382/98.11 |
| 5,852,646 A | 12/1998 | Klotz et al. | 378/8 |
| 6,404,853 B1 | 6/2002 | Odogba et al. | 378/98.8 |
| 6,623,161 B2 | 9/2003 | Aufrichtig et al. | 378/207 |
| 7,015,961 B2 * | 3/2006 | Kakarala | 348/246 |
| 2002/0087074 A1 * | 7/2002 | Nicolas et al. | 600/427 |
| 2004/0061785 A1 * | 4/2004 | Aufrichtig et al. | 348/207.99 |

* cited by examiner

Primary Examiner—Jingge Wu
Assistant Examiner—Amara Abdi
(74) Attorney, Agent, or Firm—McAndrews, Held & Malloy, Ltd.; Peter J. Vogel; Michale A. Dellapenna

(57) ABSTRACT

A system and method for asynchronous calibration of a solid-state detector are provided. A first offset is obtained with a first frame interval. A second offset image is obtained with a second frame interval that is shorter than the first frame interval. A third offset image is obtained with a third frame interval that is longer than the first frame interval. The first offset image is offset with each of the second offset image and the third offset image to produce offset comparison images. Pixels in the offset comparison images with an intensity value that exceeds an asynchronous threshold intensity value are identified as asynchronous bad pixels and added to a bad pixel map. Subsequently acquired x-ray images are offset with corresponding offset images. The bad pixel map is used to identify asynchronous bad pixels in the displayed images.

16 Claims, 3 Drawing Sheets

ASYNCHRONOUS CALIBRATION AND CORRECTION OF A SOLID-STATE DETECTOR

BACKGROUND OF THE INVENTION

The present invention generally relates to solid-state x-ray detectors. More particularly, the present invention relates to asynchronous calibration of solid-state x-ray detectors to reduce image artifacts.

Solid-state x-ray detectors have been proposed that comprise a two dimensional array of 1,000 to 4,000 detector elements in each dimension (x,y). Each detector element comprises a photo detector that detects and stores charge representative of an amount of radiation incident on the detector element. Each detector element further includes a thin film transistor (TFT) connected to the photo diode and operated as a switch to enable and disable read out of the charge stored on the photo diode. Each detector element ultimately produces an electrical signal that corresponds to the brightness of a picture element in the x-ray image projected onto the detector. The signal from each detector element is read out individually and digitized for further image processing, storage and display.

The solid-state detector may be used in a variety of x-ray medical imaging applications. Some examples of applications where solid-state detectors are used include angiographic procedures like rotational angiography and bolus chase.

During rotational angiography, a gantry supports an x-ray source on one side of a patient and a detector on the opposite side of the patient. The gantry rotates the x-ray source and the detector around the patient. At predetermined positions during the rotation, the x-ray source emits x-rays through the patient and the x-rays impinge upon the surface of the detector.

In order to associate an acquired image with a particular angular position relative to the patient, the detector is synchronized with the angular position of the gantry. For example, if images are to be acquired with every two degree rotation around the patient, the x-ray source and detector are activated with every two degree rotation of the gantry.

Because some tissues are relatively transparent to x-rays, the patient is sometimes injected with a dye that absorbs x-rays. The x-ray image acquired while the patient is injected with the dye is commonly referred to as a contrast image or an opacified image. Absorption of the x-rays by the dye makes the tissues containing the dye appear darker on the resulting x-ray image.

To further highlight the tissues containing the dye, another corresponding x-ray image taken without the dye, commonly referred to as a mask image, may be subtracted from the contrast image. Subtraction of the mask image from the contrast image results in a combined image with most of the non-dyed material removed. Such contrast and mask images are frequently used to optimize views of vascular structures, stenoses, aneurysms, tumors, and neurovascularization.

Because of physical variations between detector elements, some pixels on a contrast image or a mask image are brighter or dimmer than neighboring pixels despite being subjected to the same level of x-ray exposure. To compensate for differences in intensity between neighboring pixel elements, an offset image may be obtained.

The offset image is typically acquired by exposing the solid-state detector to a uniform level of x-ray exposure or no x-ray exposure. The offset image is then subtracted from the mask and contrast images to cancel or "zero out" some of the effects on image quality that result from physical variations between detector elements.

One of the effects arising from physical differences between detector elements is a change in pixel intensity as the time interval, or frame interval, between image acquisitions is varied. For example, the detector elements may contain residual charge from previous acquisitions and the rate of decay of the residual charge on individual detector elements may vary due to physical variations between the detector elements. Variations in decay rate of residual charge between detector elements may result in differences in the level of charge stored by the detector elements at particular moments in time. Consequently, the level of charge stored by the individual detector elements during an image acquisition may be affected by the time that has elapsed since the last image acquisition.

Because the time interval between image acquisitions from the solid-state detector affects intensity values read from the detector elements, offset images are typically acquired with frame intervals that are identical to frame intervals of corresponding contrast and mask images. The offset images are then subtracted from the contrast and mask images to cancel some of the effects of physical differences between detector elements.

Typically, a set of offset images is acquired before mask images and contrast images are obtained. The time intervals between acquisitions of the offset images are varied to match the potential frame intervals of subsequently acquired mask and contrast images. The offset images are then saved as a set of offset images with each offset image representing a particular frame interval.

After the offset images have been obtained, a first acquisition run is performed where x-ray images are obtained of a patient before dye has been injected into the patient. During the first acquisition run, the gantry will rotate the x-ray source and detector around the patient. Images are acquired at predetermined positions as the x-ray source and detector rotate around the patient.

Next, the patient is injected with dye and the gantry again rotates the x-ray source and detector around the patient. A set of contrast images is acquired at the same positions as the mask images.

Offset images are then selected from the set of offset images based upon the frame intervals of the mask and contrast images. The offset images are then subtracted from the corresponding mask and contrast images to produce offset corrected mask and contrast images that compensate for some of the variation in pixel intensity resulting from physical differences between photodetector elements. Corresponding offset corrected mask and contrast images may then be combined to produce a combined image that highlights the tissues containing the dye.

The mask and contrast runs are performed during high-speed rotation of the gantry. During the mask and contrast runs, the gantry may go through distinct phases of acceleration, constant speed, and deceleration. Because the gantry rotates at high speeds and the speed of the gantry varies during the acquisition runs, it is difficult to synchronize motion of the gantry with the detector reads. High speed and variable rotation of the gantry also makes it difficult to reproduce image acquisitions at the identical positions and frame intervals of prior image acquisition runs. Consequently, it is difficult to acquire mask and contrast images at identical positions in separate runs and it is difficult to acquire offset, mask, and contrast images with identical frame intervals.

Another type of imaging procedure that may involve acquiring offset, mask, and contrast images is a bolus chase procedure. During a bolus chase procedure, a patient is positioned on a movable platform that slides back and forth between an x-ray source and a detector. The patient is injected with a contrast agent. As the contrast agent flows through the circulatory system of the patient, the patient is incrementally moved between the x-ray source and the detector to follow the progression of the contrast agent as it passes through the circulatory system of the patient. Images of the patient and the progression of the contrast are taken at a predetermined interval of patient movement. For example, an image may be acquired every 10 centimeters as the patient slides between the x-ray source and detector.

The rate of patient movement between the x-ray source and the detector depends on the rate at which the contrast flows through the circulatory system of the patient. Because the contrast may flow through different portions of the patient at different rates, the rate of movement of the patient between the x-ray source and the detector may vary accordingly. Consequently, the time intervals between acquisitions of the x-ray images may vary because the time for a patient to move a predetermined interval may vary.

Often, a radiologist or technician is in control of the table speed and is present to view images in real time. Because the radiologist or technician may be diagnosing a patient during the procedure, offset images are used to reduce undesirable pixel variations in images displayed during the procedure in order to provide a more accurate and immediate diagnosis. Thus, for a bolus chase procedure, the offset images are typically acquired prior to acquisition of contrast or mask images so the contrast and mask images may be offset corrected and displayed during the procedure.

However, because the offset images are acquired prior to the x-ray images, the various frame intervals of the x-ray images may not be known when the offset images are acquired. Consequently, the frame intervals of the offset images may not match-up with the frame intervals of the x-ray images obtained during a bolus chase procedure.

As presented earlier, variations in the time interval between image acquisitions may produce variations in pixel intensities. Thus, an offset image representing one frame interval may have different pixel intensity values than another offset image representing another frame interval despite being subjected to the same level of x-ray exposure. Consequently, an x-ray image obtained at a particular frame interval following the last x-ray image acquisition should be offset corrected with an offset image representing the same particular frame interval. Otherwise, if the x-ray image is offset corrected with an offset image representing a different frame interval, the resulting asynchronous combination may still include the effects on pixel intensity caused by variations in frame interval. Variations in pixel intensity in an offset corrected image resulting from an asynchronous combination of images obtained at different frame intervals may appear in final images as temporal artifacts.

Thus, it may be highly desirable to have a system that determines the effect of variations in frame intervals upon the level of charge stored by photodetector elements. It may also be desirable to have a system that determines which pixels show an unacceptable risk for becoming a temporal artifact in a final image because of real time variations in frame intervals and compensates for temporal artifact causing pixels to produce a final image with less image artifacts.

BRIEF SUMMARY OF THE INVENTION

A preferred embodiment of the present invention provides a system for asynchronous calibration and correction of a solid-state detector by identifying the effects of variations in frame interval upon photodetector elements of a solid-state detector and reducing the appearance of temporal artifacts in an x-ray image.

During asynchronous calibration and correction of the solid-state detector, a first offset image is obtained with a first interval of time between the acquisition of the first offset image and another image immediately preceding the acquisition of the first offset image. A second offset image is obtained with a second interval of time between the acquisition of the second offset image and another image immediately preceding the acquisition of the second offset image. The first offset image is offset with the second offset image to produce an offset comparison image. The offset comparison image is analyzed to determine the effect of variations in frame interval upon the intensity of pixels in acquired images. Pixels in the offset comparison image that exceed an asynchronous threshold intensity value are identified as asynchronous bad pixels and added to a bad pixel map.

The x-ray frame interval of an x-ray image is used to access the bad pixel map and identify asynchronous bad pixels for that particular x-ray frame interval. Asynchronous bad pixels in the x-ray image are then corrected in the final x-ray image to reduce the appearance of temporal artifacts.

DETAILED DESCRIPTION OF THE INVENTION

Figure 1:
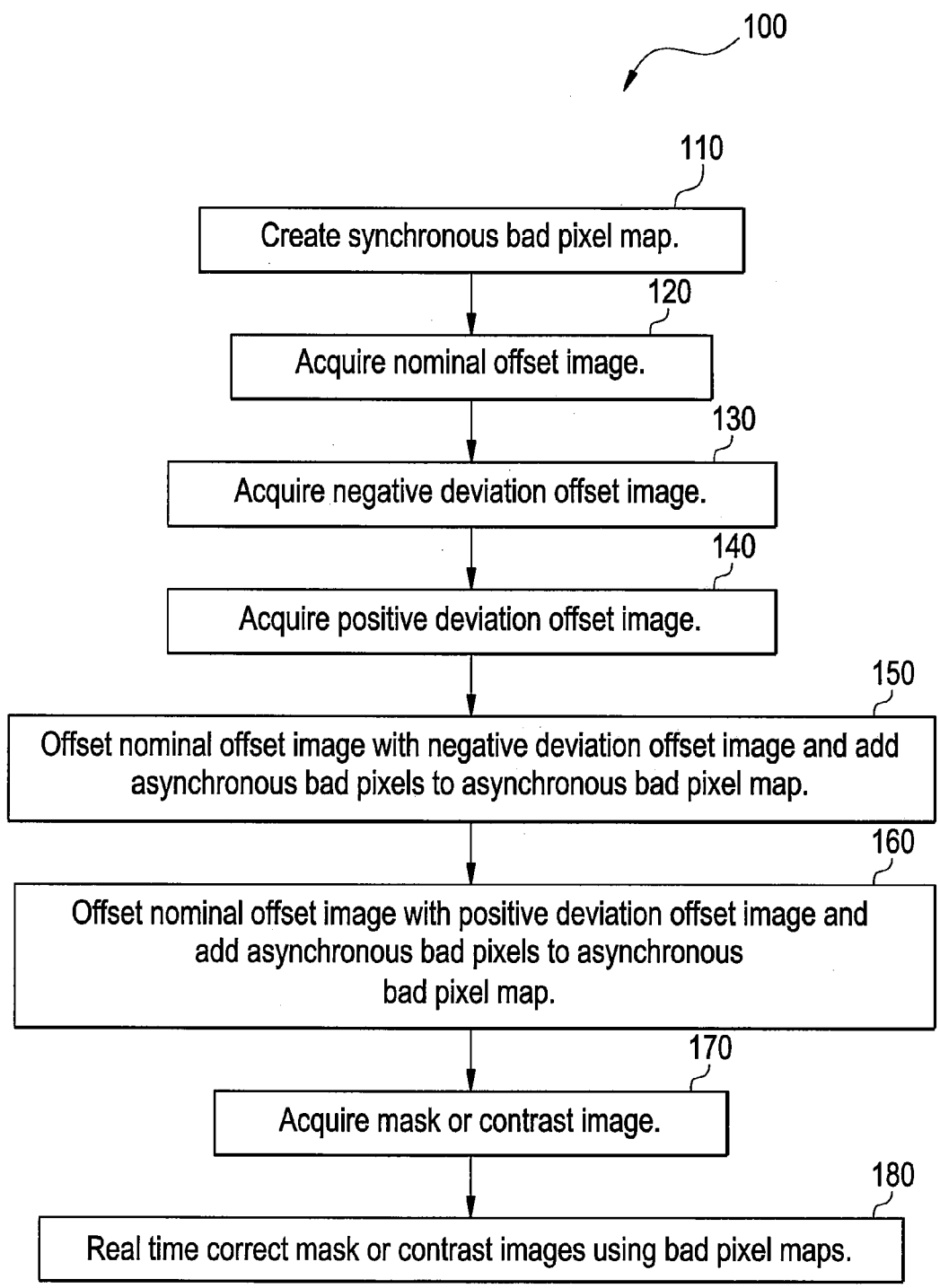
FIG. 1 shows a block diagram for a system for asynchronous calibration and correction of a solid-state detector in accordance with an embodiment of the present invention.

FIG. 1 shows a block diagram of an asynchronous calibration system 100 for a solid-state detector in accordance with an embodiment of the present invention. The asynchronous calibration system 100 illustrated in FIG. 1, includes steps 110, 120, 130, 140, 150, 160, 170, and 180.

In step 110, a synchronous bad pixel map is constructed from synchronous image data received at a solid-state detector. The synchronous bad pixel map is constructed using typical methods already known in the industry for constructing synchronous bad pixel maps.

For example, an offset image is obtained by reading the detector at a predetermined acquisition time interval without exposing the detector to x-rays. The offset image is then analyzed to determine which detector elements of the solid-state detector have extreme levels of dark current in relation to the other detector elements of the solid-state detector. For example, the intensity values of the detector elements of the solid-state detector are used to determine a synchronous threshold intensity value. Intensity values for detector elements that exceed the synchronous threshold intensity value are considered to represent extreme levels of dark current. The detector elements that represent extreme levels of dark current are designated as synchronous bad pixels. The synchronous bad pixels are then added to a synchronous bad pixel map that identifies bad pixels with an affinity for exhibiting extreme levels of dark current.

Also, the synchronous bad pixel map may be constructed using images obtained during uniform x-ray exposure. Like the dark images, the offset images obtained with uniform x-ray exposure are then analyzed to determine which detector elements produce extreme pixel intensity values in relation to the pixel intensity values of the other detector elements. The detector elements that present extreme pixel intensity values in relation to the pixel intensity values of the other detector elements are also designated as synchronous bad pixels. The synchronous bad pixels are then added to the synchronous bad pixel map.

In step 120, a nominal offset image is acquired. During acquisition of the nominal offset image, the solid-state detector is not exposed to x-rays. Pixel intensity values are read from the solid-state detector with a nominal image frame interval between image acquisitions. The nominal image frame interval is selected to match the frame interval between the acquisitions of corresponding contrast and mask images.

In step 130, a negative deviation offset image is acquired. During acquisition of the negative deviation offset image, the solid-state detector is not exposed to x-rays. Pixel intensity values are read from the solid-state detector with a negative deviation frame interval that is slightly shorter than the nominal image frame interval of the nominal offset image. For example, the negative deviation frame interval may be selected to be ten percent shorter than the nominal image frame interval.

In step 140, a positive deviation offset image is acquired. During acquisition of the positive deviation offset image, the solid-state detector is not exposed to x-rays. Pixel intensity values are read from the solid-state detector with a positive deviation frame interval that is slightly longer than the nominal image frame interval of the nominal offset image. For example, the positive deviation frame interval may be selected to be ten percent longer than the nominal image frame interval.

In step 150, the nominal offset image is offset with the negative deviation offset image. Pixel values that exceed an asynchronous threshold intensity value may be designated as asynchronous bad pixels and added to an asynchronous bad pixel map.

In one embodiment of the present invention, the asynchronous threshold intensity value is based upon a contrast-to-noise ratio. The asynchronous threshold intensity value is set to a value of the contrast-to-noise ratio at which a variation in pixel intensity between the pixel and surrounding pixels is perceived to be unacceptable. Intensity values for detector elements that exceed the asynchronous threshold intensity value are considered overly sensitive or insensitive to variations in the time interval between image acquisitions. The overly sensitive or insensitive detector elements are designated as asynchronous bad pixels. The asynchronous bad pixels are then added to an asynchronous bad pixel map.

In step 160, the nominal offset image is offset with the positive deviation offset image. Pixel values that exceed an asynchronous threshold intensity value may be designated as asynchronous bad pixels and added to an asynchronous bad pixel map.

In step 170, an x-ray image is acquired. The x-ray image is acquired while the solid-state detector is exposed to x-rays. Intensity values are read from the solid-state detector with an x-ray image frame interval between image acquisitions.

In step 180, the x-ray image is real-time corrected using the synchronous and asynchronous bad pixel maps. Asynchronous bad pixels are identified in the x-ray image by accessing the asynchronous bad pixel map and determining which pixels are identified as asynchronous bad pixels for a nominal image frame interval equal to the x-ray image frame interval.

In an alternative embodiment, the synchronous bad pixel map and asynchronous bad pixel map be combined into a combined bad pixel map. The combined bad pixel map is then used to correct x-ray images rather than the separate synchronous bad pixel map and asynchronous bad pixel map.

In another alternative embodiment, the nominal offset image, the negative deviation offset image, and the positive deviation offset image are acquired while exposing the solid-state detector to a uniform level of x-rays. Steps 120 through 180 are then repeated using the nominal offset image, the negative deviation offset image, and the positive deviation offset image acquired with uniform x-ray exposure in place of the nominal offset image, the negative deviation offset image, and the positive deviation offset image acquired without x-ray exposure.

Figure 2:
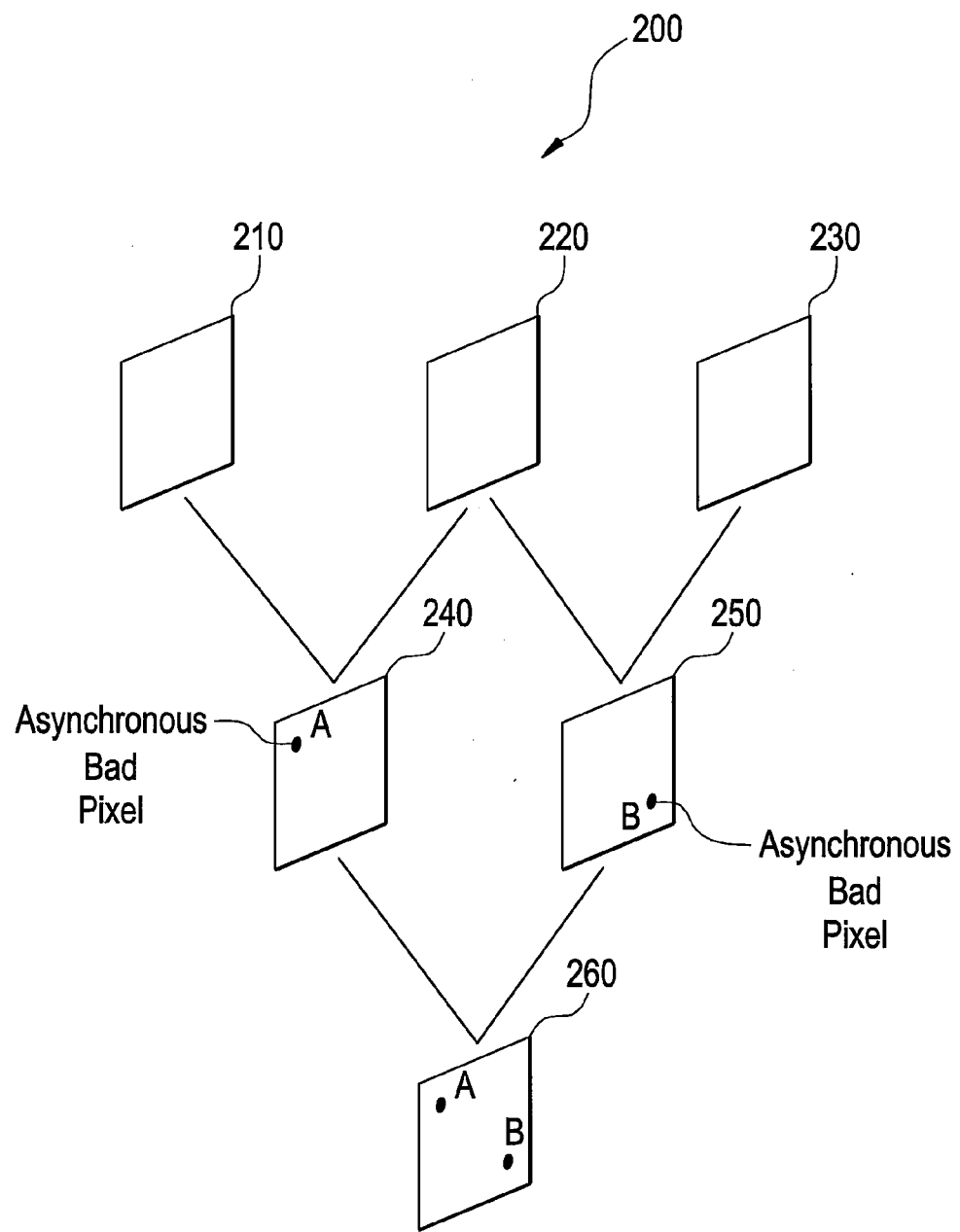
FIG. 2 illustrates a system for constructing an asynchronous bad pixel map in accordance with an embodiment of the present invention.

FIG. 2 illustrates a system 200 for constructing an asynchronous bad pixel image 260 in accordance with an embodiment of the present invention. The system 200 includes nominal offset image 220, negative deviation offset image 210, positive deviation offset image 230, negative offset comparison image 240, positive offset comparison image 250, and asynchronous bad pixel map 260.

In operation, a nominal offset image 220 is acquired. During acquisition of the nominal offset image 220, the solid-state detector is not exposed to x-rays. Pixel intensity values are read from the solid-state detector with a nominal image frame interval between image acquisitions. The nominal image frame interval is selected to match the x-ray image frame interval of corresponding x-ray images.

A negative deviation offset image 210 is acquired. During acquisition of the negative deviation offset image 210, the solid-state detector is not exposed to x-rays. Pixel intensity values are read from the solid-state detector at a negative deviation frame interval that is slightly shorter than the nominal image frame interval of the nominal offset image 220. For example, as shown in FIG. 2, the negative deviation frame interval may be selected to be ten percent shorter than the nominal image frame interval. In this example, if the nominal image frame interval is represented by a value X, then the negative deviation frame interval would be 0.9 times X.

A positive deviation offset image 230 is acquired. During acquisition of the positive deviation offset image 230, the solid-state detector is not exposed to x-rays. Pixel intensity values are read from the solid-state detector at a positive deviation frame interval that is slightly longer than the nominal image frame interval of the nominal offset image 220. For example, as shown in FIG. 2, the positive deviation frame interval may be selected to be ten percent longer than the nominal image frame interval. In this example, if the nominal image frame interval is represented by a value X, then the positive deviation frame interval would be 1.1 times X.

The nominal offset image 220 is offset with the negative deviation offset image 210 to produce a negative offset comparison image 240. Pixel values in the negative offset comparison image 240 that exceed an asynchronous threshold intensity value are designated as asynchronous bad pixels. For example, in the negative offset comparison image 240, the pixel A is identified as an asynchronous bad pixel. Because the pixel A is identified as an asynchronous bad pixel, the pixel A is added to the asynchronous bad pixel map 260.

Similarly, the nominal offset image 220 is offset with the positive deviation offset image 230 to produce a positive offset comparison image 250. Pixel values in the positive offset comparison image 250 that exceed an asynchronous threshold intensity value are designated as asynchronous bad pixels. For example, in the positive offset comparison image 250, the pixel B is identified as an asynchronous bad pixel. Because the pixel B is identified as an asynchronous bad pixel, the pixel B is added to the asynchronous bad pixel map 260.

While the description of FIG. 2 above focuses upon adding bad pixels for a desired frame interval to an asynchronous bad pixel map, bad pixels for a plurality of frame intervals may be added to the asynchronous bad pixel map. The plurality of frame intervals may be selected to span the range of frame intervals experienced by a solid-state detector during the imaging process. Thus, the asynchronous bad pixel map may be accessed to identify and correct pixels that have an affinity for being bad pixels at a specific frame interval.

In an alternative embodiment, the nominal offset image 220, the negative deviation offset image 210, and the positive deviation offset image 230 are acquired while exposing the solid-state detector to a uniform level of x-rays. The nominal offset image 220 is then offset with the negative deviation offset image 210 and the positive deviation offset image 230 to identify asynchronous bad pixels.

Figure 3:
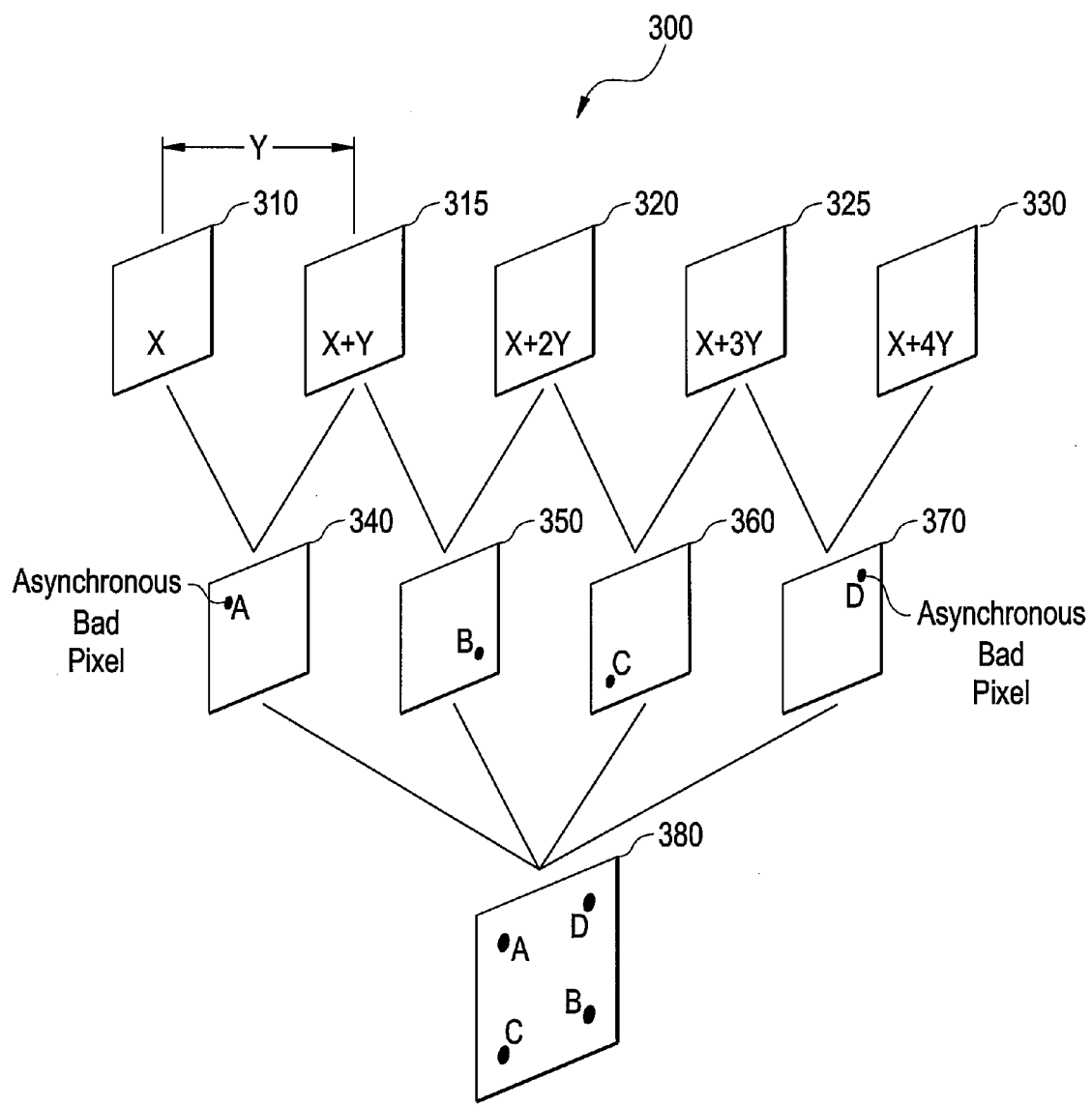
FIG. 3 illustrates a system for constructing an asynchronous bad pixel map in accordance with an embodiment of the present invention.

FIG. 3 illustrates a system 300 for identifying asynchronous bad pixels at a plurality of frame intervals and adding the asynchronous bad pixels to an asynchronous bad pixel map. The system 300 includes a first offset image 310, a second offset image 315, a third offset image 320, a fourth offset image 325, a fifth offset image 330, a first offset comparison image 340, a second offset comparison image 350, a third offset comparison image 360, a fourth offset comparison image 370, an asynchronous bad pixel map 380.

In operation, the offset images 310, 315, 320, 325 and 330 are acquired at different equally spaced frame intervals. In FIG. 3, the time between frame intervals is labeled as Y. The first offset image 310 is acquired with a frame interval of X. The second offset image 315 is acquired with a frame interval of X+Y. The third offset image 320 is acquired with a frame interval of X+2Y. The fourth offset image 325 is acquired with a frame interval of X+3Y. The fifth offset image 330 is acquired with a frame interval of X+4Y.

To add a set of asynchronous bad pixels for a frame interval of X+Y to the asynchronous bad pixel map 380, the second offset image 315, which is obtained at a frame interval of X+Y, is offset with neighboring offset images that are obtained at the next longest and the next shortest frame intervals. As illustrated in FIG. 3, the first offset image 310 has the next shortest frame interval to that of the second offset image 315 and the third offset image 320 has the next longest frame interval to that of the second offset image 315.

When the first offset image 310 and the third offset image 320 are individually offset with the second offset image 315, the first offset comparison image 340 and the second offset comparison image 350 are produced, respectively. Pixel values in the first offset comparison image 340 and the second offset comparison image 350 that exceed the asynchronous threshold intensity value are designated as asynchronous bad pixels and added to the asynchronous bad pixel map 380.

For example, in the first offset comparison image 340, the pixel A is identified as an asynchronous bad pixel. In the second offset comparison image 350, the pixel B is identified as an asynchronous bad pixel. Because the pixels A and B are identified as asynchronous bad pixels, the pixels A and B are added to the asynchronous bad pixel map 380.

Likewise, to add a set of asynchronous bad pixels for a frame interval of X+3Y to the asynchronous bad pixel map 380, the fourth offset image 325 is offset with neighboring offset images that are obtained with the next longest and the next shortest frame intervals. As illustrated in FIG. 3, the third offset image 320 has the next shortest frame interval to that of the fourth offset image 325 and the fifth offset image 330 has the next longest frame interval to that of the fourth offset image 325.

When the third offset image 320 and the fifth offset image 330 are individually offset with the fourth offset image 325, the third offset comparison image 360 and the fourth offset comparison image 370 are produced, respectively. Pixel values in the third offset comparison image 360 and the fourth offset comparison image 370 that exceed the asynchronous threshold intensity value are designated as asynchronous bad pixels. Pixel values in the third offset comparison image 360 and the fourth offset comparison image 370 that exceed the asynchronous threshold intensity value are designated as asynchronous bad pixels and added to the asynchronous bad pixel map 380.

For example, in the third offset comparison image 360, the pixel C is identified as an asynchronous bad pixel. In the fourth offset comparison image 370, pixel D is identified as an asynchronous bad pixel. Because the pixels C and D are identified as asynchronous bad pixels, the pixels C and D are added to the asynchronous bad pixel map 380.

To add additional sets of asynchronous bad pixels for additional frame intervals, a process similar to that described above for a frame interval of X+Y and a frame interval of X+3Y is performed. If an asynchronous bad pixel image is desired for a particular frame interval, an offset image is obtained with the desired frame interval and an offset image with a shorter frame interval and a longer frame interval are obtained. The offset image with the desired frame interval is offset individually with the offset images obtained with the shorter and longer frame intervals. Pixels in the resulting offset comparison images with an intensity value exceeding the asynchronous threshold intensity value are added to the asynchronous bad pixel map 380.

When an x-ray image is obtained with a particular frame interval during an x-ray procedure, the asynchronous bad pixels corresponding to the frame interval of the x-ray image are identified from the asynchronous bad pixel map and corrected.

Thus, the effects of real time variations in frame interval between x-ray images and offset images may be reduced. For example, before x-ray images are obtained during a bolus chase procedure, offset images may be obtained with a plurality of frame intervals. Each offset image obtained may be offset with an offset image obtained with a slightly shorter frame interval and an offset image obtained with a slightly longer frame interval. Pixels in the resulting offset comparison images that exceed an asynchronous threshold intensity value are added to an asynchronous bad pixel map.

The asynchronous threshold intensity value may be determined based upon user perception studies. For example, users of imaging equipment may be asked to view various offset comparison images and identify which pixels appear to be bad pixels. Users may perceive pixels to be bad pixels based upon differences between a pixel and other surrounding pixels or based upon a particular contrast to noise ratio. The intensity values of the pixels identified during the perception studies may then be used to determine a value at which a user typically no longer identifies a pixel as a bad pixel. This intensity value may be used as the asynchronous threshold intensity value.

During the bolus chase procedure, x-ray images may be obtained with a plurality of frame intervals. As each x-ray image is obtained, each x-ray image is offset with a stored offset image. Using the frame interval of the x-ray image, the asynchronous bad pixel map may be accessed and pixels flagged as asynchronous bad pixels for that frame interval may be identified. The pixels identified as bad pixels may then be corrected using standard image correction procedures such as interpolation or weighting.

Thus, the systems presented determine the effect of variation in frame intervals upon the level of charge stored by detector elements. The systems presented also determine which pixels show an unacceptable risk for becoming a temporal artifact and compensate for temporal artifact causing pixels.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for reducing the appearance of bad pixels in an x-ray image including:
    acquiring a first offset image with a first frame interval;
    identifying synchronous bad pixels based on comparison of pixel values in said first offset image to a synchronous threshold intensity value;
    creating a synchronous bad pixel map including synchronous bad pixels identified from said first offset image;
    acquiring a second offset image with a second frame interval, said second frame interval being shorter than said first frame interval;
    acquiring a third offset image with a third frame interval, said third frame interval being longer than said first frame interval;
    offsetting said first offset image with said second offset image to produce a first offset comparison image;
    identifying asynchronous bad pixels in said first offset comparison image;
    offsetting said first offset image with said third offset image to produce a second offset comparison image;
    identifying asynchronous bad pixels in said second offset comparison image; and
    creating an asynchronous bad pixel map including said asynchronous bad pixels identified in said first offset comparison image and said second offset comparison image.

2. The method of claim 1 wherein pixel intensity values of said asynchronous bad pixels exceed an asynchronous threshold intensity value.

3. The method of claim 2 wherein said asynchronous threshold intensity value is a contrast to noise ratio.

4. The method of claim 1 wherein pixel intensity values of said synchronous bad pixels exceed a synchronous threshold intensity value.

5. The method of claim 1 wherein said synchronous bad pixel map and said asynchronous bad pixel map comprise a bad pixel map, wherein said bad pixel map includes asynchronous bad pixels and synchronous bad pixels.

6. A method for reducing the appearance of bad pixels in an x-ray image including:
    acquiring a plurality of offset images with a plurality of frame intervals;
    selecting a first offset image from said plurality of offset images, wherein said first offset image was acquired with a first frame interval;
    selecting a second offset image from said plurality of offset images, wherein said second offset image was acquired with a shorter frame interval than said first frame interval;
    selecting a third offset image from said plurality of offset images, wherein said third offset image was acquired with a longer frame interval than said first frame interval;
    identifying synchronous bad pixels in said first offset image;
    offsetting said first offset image with said second offset image to produce a first offset comparison image;
    offsetting said first offset image with said third offset image to produce a second offset comparison image; and
    identifying asynchronous bad pixels in said first offset comparison image and said second offset comparison image.

7. The method of claim 6 wherein pixel intensity values of said asynchronous bad pixels exceed an asynchronous threshold intensity value.

8. The method of claim 7 wherein said asynchronous threshold intensity value is a contrast to noise ratio.

9. The method of claim 6 including adding said asynchronous bad pixels to an asynchronous bad pixel map.

10. The method of claim 9 including:
    acquiring an x-ray image with a frame interval between the frame intervals of said second offset image and said third offset image;
    offsetting said x-ray image with said first offset image to produce an offset x-ray image;
    identifying potential asynchronous bad pixels in said offset x-ray image using said asynchronous bad pixel map; and
    modifying said potential asynchronous bad pixels in said offset x-ray image.

11. The method of claim 10 wherein said asynchronous bad pixel map includes asynchronous bad pixels identified from a plurality of offset comparison images.

12. The method of claim 10 wherein said potential asynchronous bad pixels identified using said asynchronous bad pixel map are associated with said first frame interval of said first offset image.

13. The method of claim 1 wherein pixel intensity values of said synchronous bad pixels exceed a threshold intensity value.

14. The method of claim 10 including adding said synchronous bad pixels to a synchronous bad pixel map.

15. The method of claim 14 including:
    identifying potential synchronous bad pixels in said offset x-ray image using said synchronous bad pixel map; and
    modifying said potential synchronous bad pixels in said offset x-ray image.

16. The method of claim 1 including:
    acquiring an x-ray image;
    offsetting said x-ray image with said first offset image to produce an offset x-ray image;
    identifying potential bad pixels in said offset x-ray image using said synchronous pixel map and said asynchronous pixel map; and
    modifying said potential bad pixels in said offset x-ray image.

* * * * *